(12) United States Patent
Kawde et al.

(10) Patent No.: US 9,362,600 B2
(45) Date of Patent: Jun. 7, 2016

(54) CELL WITH REUSABLE AND DISPOSABLE ASSEMBLIES FOR SIMULTANEOUS ELECTROCHEMICAL AND EPR MEASUREMENTS

(71) Applicant: KING FAHD UNIVERSITY OF PETROLEUM AND MINERALS, Dhahran (SA)

(72) Inventors: Abdel-Nasser Metwally Aly Kawde, Dhahran (SA); Mohamed Aly Morsy, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 527 days.

(21) Appl. No.: 14/023,468

(22) Filed: Sep. 11, 2013

(65) Prior Publication Data

US 2015/0068899 A1    Mar. 12, 2015

(51) Int. Cl.
*H01M 14/00* (2006.01)
*G01N 27/403* (2006.01)
(Continued)

(52) U.S. Cl.
CPC ............. *H01M 14/00* (2013.01); *G01N 24/10* (2013.01); *G01N 27/403* (2013.01); *G01N 27/416* (2013.01); *G01R 33/30* (2013.01); *Y10T 29/4911* (2015.01)

(58) Field of Classification Search
CPC . G01N 24/10; G01N 27/403; G01N 27/4035; G01N 27/416; G01N 33/48714; G01N 27/333; G01N 27/36
See application file for complete search history.

(56) References Cited

U.S. PATENT DOCUMENTS 4,486,290 A * 12/1984 Cahalan ............. G01N 27/4035
                                                        204/414
4,978,921 A * 12/1990 Indig ...................... G21C 17/10
                                                        204/400
(Continued)

FOREIGN PATENT DOCUMENTS

CN          102560527 A      7/2012
FR          2626676 A1       8/1989
GB          922624           4/1963

OTHER PUBLICATIONS

Elsevier, R.N. Bagchi, A.M. Bond, The Bubble Electrode—A New Electrode for the Combination of Voltammetry, Electrolysis and Electron Spin Resonance Spectroscopy, pp. 105-112, 1988, Journal of Electroanalytical Chemistry.

(Continued)

*Primary Examiner* — Jill Warden
*Assistant Examiner* — Matthew Krcha
(74) *Attorney, Agent, or Firm* — Richard C. Litman

(57) ABSTRACT

A cell and method for simultaneous electrochemical and EPR measurements, including a disposable assembly, allows for a single device to produce data for both electroanalysis and EPR spectroscopy by generating a Redox reaction to form free radicals. The cell includes first and second hollow tubes, with the second tube being removably insertable into the first hollow tube. The interior of the first tube contains an insulating material, an electro-conductive material, and a wire connector extending from the electro-conductive material and out the first tube. The interior of the second tube contains an electrolytic solution, an analyte, a working electrode, and insulating material surrounding the working electrode. The second tube is inserted into the first tube and a reference electrode is placed into the second tube. The cell is placed within an EPR spectrometer. A potential is applied to the reference electrode to generate the Redox reaction of the analyte.

18 Claims, 5 Drawing Sheets

(51) Int. Cl.
  *G01N 27/416* (2006.01)
  *G01N 24/10* (2006.01)
  *G01R 33/30* (2006.01)

(56) References Cited

U.S. PATENT DOCUMENTS

| | | | |
|---|---|---|---|
| 5,066,372 A | 11/1991 | Weetall | |
| 6,322,680 B1 * | 11/2001 | Itsygin | G01N 27/4035 204/416 |
| 6,391,646 B1 | 5/2002 | Khangulov | |
| 6,783,645 B2 | 8/2004 | Cheng et al. | |
| 7,556,724 B2 | 7/2009 | Huang | |
| 8,187,446 B2 | 5/2012 | Huang | |
| 2011/0048971 A1 * | 3/2011 | Bower | G01N 27/4035 205/787.5 |
| 2012/0103807 A1 | 5/2012 | Dattelbaum et al. | |

OTHER PUBLICATIONS

Elsevier, Y. Harima, T. Eguchi, K. Yamashita, K. Kojima, M. Shiotani, An in situ ESR study on poly(3-methylthiophene): charge transport due to polarons and bipolarons before the evolution of metallic conduction, pp. 121-128, 1999, Synthetic Materials 105.

Elsevier, Murray et al., An in situ electrochemical cell for Q- and W-band EPR Spectroscopy, pp. 206-209, 2011, Journal of Magnetic Resonance.

* cited by examiner

CELL WITH REUSABLE AND DISPOSABLE ASSEMBLIES FOR SIMULTANEOUS ELECTROCHEMICAL AND EPR MEASUREMENTS

BACKGROUND OF THE INVENTION

1. Field of the Invention

The present invention relates to pharmacological analysis, and particularly to a disposable device capable of producing simultaneous electrochemical and electron paramagnetic resonance spectroscopic measurements.

2. Description of the Related Art

As medicine continues to advance, the analysis of medications is becoming a more significant component as to safer drugs. Analytical chemistry, the field of analyzing the separation, identification, and quantification of chemical compounds, is providing a path for more effective and safer drugs. Two common instrumental methods used in analytical chemistry laboratories are Spectroscopy and Electrochemical analysis.

Spectroscopy is a technique measuring an electromagnetic radiation component that is emitted, absorbed, or scattered by the material being analyzed. Spectroscopy in the pharmaceutical arena can be used to determine impurities of a drug, characterize the composition of a compound, and investigate the interaction of drug metabolites in bodily fluids. Spectroscopy based on measuring microwave absorption includes a technique called Electron Paramagnetic Resonance (EPR), also known in the field as Electron Spin Resonance (ESR).

EPR spectroscopy works by analyzing the unpaired electrons of a sample. A sample of the compound to be tested is placed within a cavity of the EPR Spectrometer surrounded by electromagnets. As a negatively charged electron spins, also referred to as "resonated", a random magnetic moment is created. When a magnetic field is applied by the surrounding electromagnets, the magnetic field forces the random magnetic moments to line up with the magnetic field. A microwave generator, typically referred to as a Klystron, then pulses the sample with a short burst of waves. These microwaves are absorbed and transmitted through the sample to a receiver on the other end that detects the signal from the sample.

EPR spectroscopy is ideal for any sample that contains unpaired electrons, often referred to as being "paramagnetic" species. Such paramagnetic species include transition metal ions, biradicals, and triplet excited states of diamagnetic molecules. EPR spectroscopy is also ideal for oxidation and reduction reactions, i.e. Redox reactions, where electrons are either added or removed.

Electrochemical analysis, also referred to as electroanalysis, can be of various different forms and types. One such technique is Voltammetry. Voltammetry is a method of determining the chemical makeup of a sample substance by measuring electrical activity, or the accumulation of chemicals, on electrodes placed in the substance. In a two electrode setup, the electrochemical cell generally has a working electrode, a reference electrode, a supporting electrolyte, and an analyte. The analyte is the substance whose properties are measured or analyzed. The working electrode makes contact with the analyte and the reference electrode applies a desired potential in a controlled manner which facilitates the transfer of charge to and from the analyte.

Various issues can arise in using an EPR spectroscopy process for pharmacological analysis that can make EPR spectroscopy relatively prohibitive. If the sample to be analyzed isn't already in a paramagnetic state, then the sample needs to be prepared to be in such paramagnetic state prior to insertion into an EPR spectrometer. Further, if the sample needs preparation via a Redox reaction using an electrochemical cell, other issues can arise. These issues include the type of electrode employed in the electrochemical cell, placement of the cell within the EPR Spectrometer, the complex arrangement of the electrochemical cell, and a relatively prohibitive cost of replacing electrochemical cells for each new electrochemical reaction and analysis, for example.

If a sample is prepared through a Redox reaction, the electrochemical reaction occurs inside the spectroscopic cell as opposed to outside the cell. A benefit of having the electrochemical reaction within the spectroscopic cell is that less stable radicals are typically not lost in the transferring process from one cell to the other. Known electrochemical cells are generally structured in a relatively complex arrangement of multiple compartments with multiple electrodes. Multiple compartments generally increase the surface area of the cell, and thereby can limit the ability to insert the cell into resonator cavities of EPR spectrometers. Further, multiple compartments and multiple electrodes can increase the cost of each cell since more material is typically being used for the cell. Also, a clean cell is desirable for each analysis and, a new cell is therefore desirable in this regard for each analysis to assist in avoiding contamination and to reduce the likelihood of unreliable results for the analysis. Further, replacing these cells time and time again can be relatively costly.

Known electrochemical cells employ base metals and precious metals as the working electrode. While these types of materials can produce the requisite oxidation needed, the oxidation values that are produced are usually not as significant as compared to other electrodes made from different materials. Further, using materials, such as copper and silver, as the working electrode can increase the cost of the electrochemical cell because of the relatively high costs of these raw materials.

It is therefore desirable that a cell used in EPR spectroscopy analysis generate a Redox reaction that also produces optimum oxidation yields, can be used within an EPR spectrometer, is relatively simple to implement, can additionally provide electrochemical analysis, and can be more cost effective as to replacement cells.

Thus, a disposable cell for simultaneous electrochemical and EPR measurements addressing the aforementioned problems is desired.

SUMMARY OF THE INVENTION

Embodiments of a cell with reusable and disposable assemblies for simultaneous electrochemical and EPR measurements provides data for both electron paramagnetic resonance spectroscopy and electrochemical analysis. The cell prepares a diamagnetic sample into a paramagnetic sample having free radicals by inducing a Redox reaction of the analyte to be tested. The cell includes a first hollow tube assembly having an upper portion and a lower portion. The lower portion of the first hollow tube is insulated with a first insulating material. A wire connector extends through the first insulating material and engages an electro-conductive material.

Embodiments of the cell for simultaneous electrochemical and EPR measurements also include a second hollow tube assembly that can be disposable by being removable and insertable into the interior of the first hollow tube. The second hollow tube assembly includes a second hollow tube having an upper and lower portion, with a working electrode inserted into the lower portion and extending into the interior of the second hollow tube. The lower portion of the second hollow tube is insulated by a second insulating material, which holds the working electrode in place and insulates the surrounding area of the lower portion. Within the interior of the second hollow tube an electrolytic solution and the analyte is placed. The electrolytic solution assists in promoting the Redox reaction of the analyte.

When the second hollow tube assembly is placed within the interior of the first hollow tube assembly, the working electrode extending out from the lower portion of the second hollow tube engages the electro-conductive material located within the lower portion of the first hollow tube. By positioning the second hollow tube of the second hollow tube assembly into the first hollow tube of the first hollow tube assembly, a cell is formed. A reference electrode is then placed into the upper portion of the second hollow tube.

The cell is placed within an EPR spectrometer. A potential voltage is applied across the reference electrode which then fuels the Redox reaction. The Redox reaction generates the free radicals that are analyzed by the EPR spectrometer. The EPR spectrometer will then generate EPR responses of the free radicals. A measuring device is also connected to the free end of the wire connector extending from the first hollow tube. The measuring device also provides electrochemical analysis by measuring both the accumulation voltage and the current from the working electrode that is produced by the Redox reaction.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
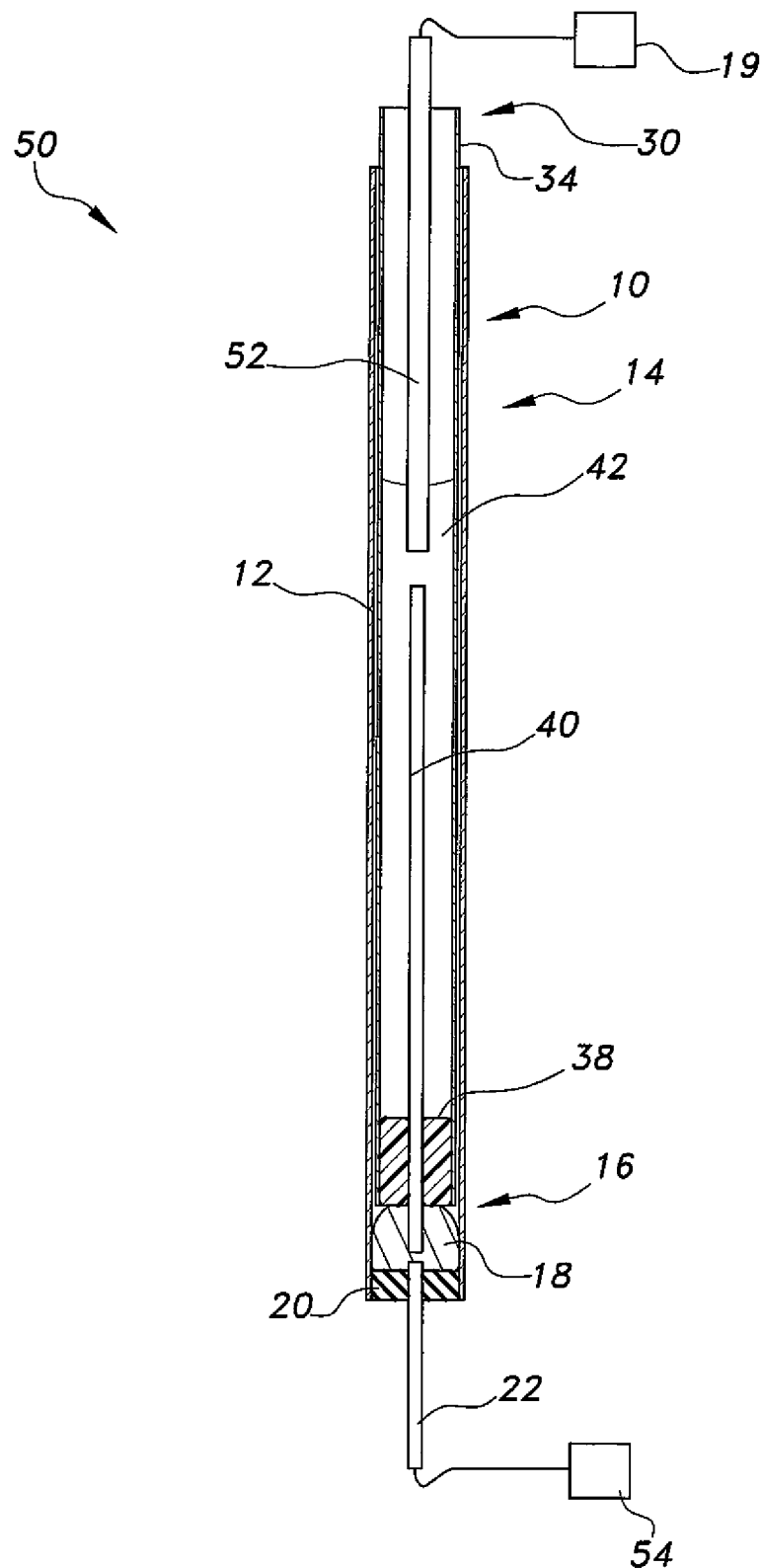
FIG. 1 is a schematic sectional front view of an embodiment of a cell having a reusable assembly as a reusable holder and a disposable assembly for simultaneous electrochemical and EPR measurements according to the present invention.
Figure 2:
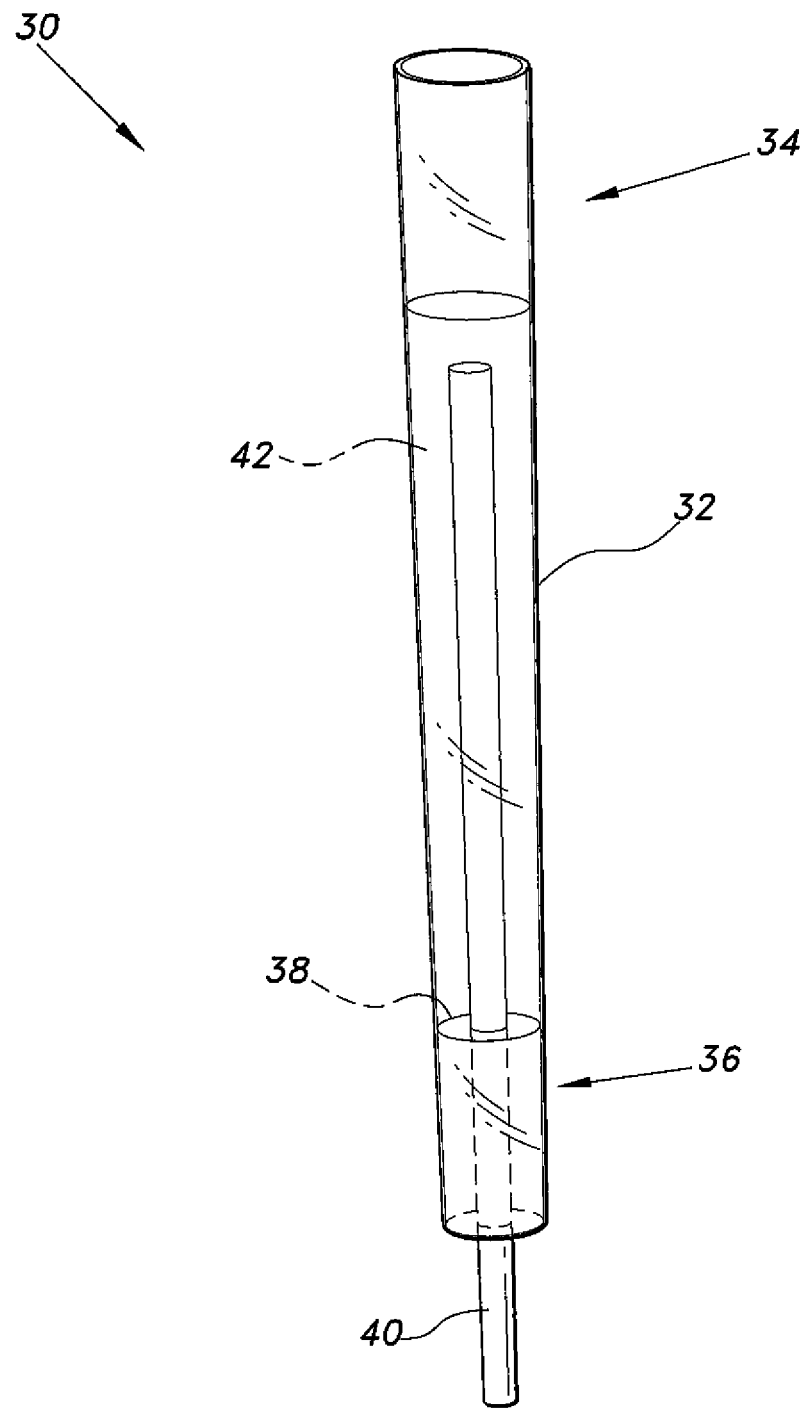
FIG. 2 is a perspective view of an embodiment of a disposable assembly of a cell for simultaneous electrochemical and EPR measurements according to the present invention.
Figure 3:
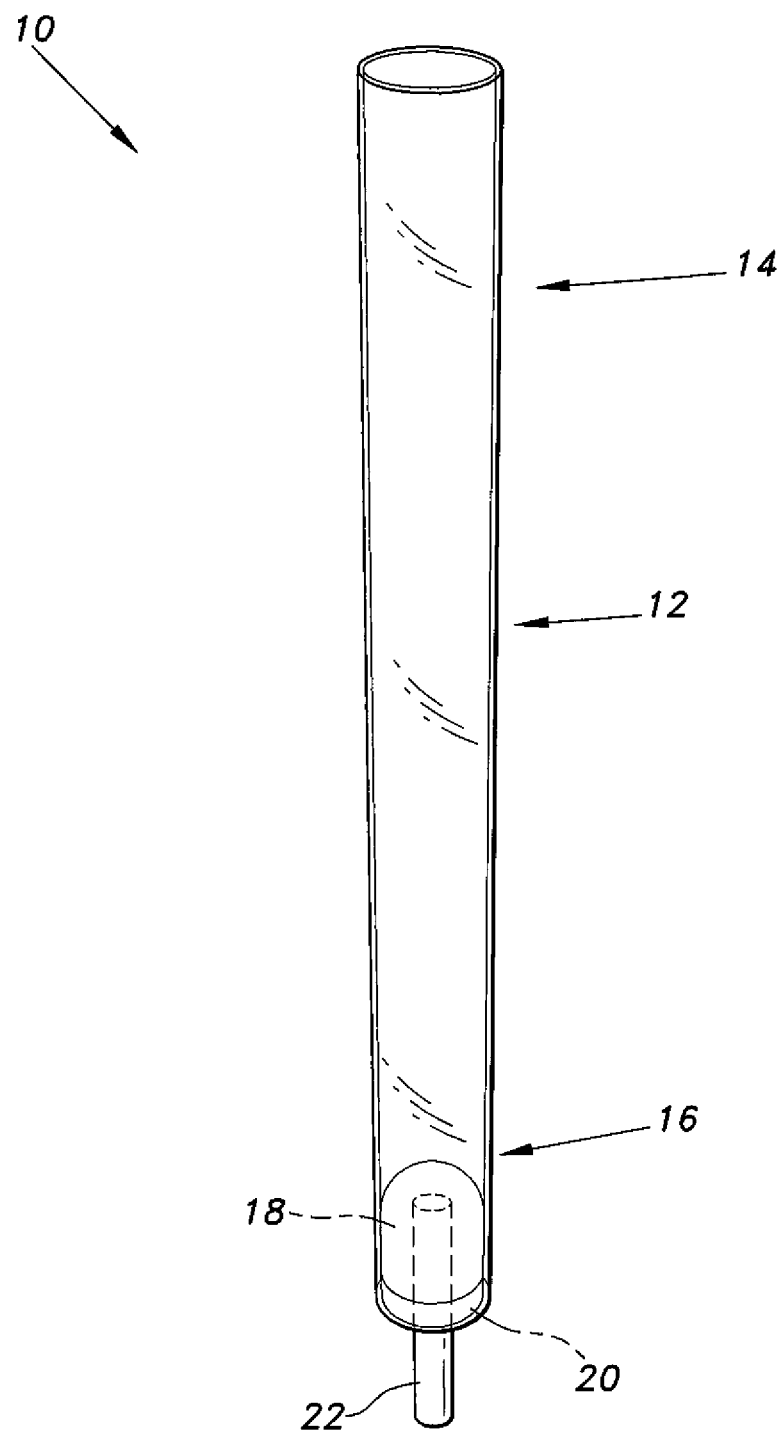
FIG. 3 is a perspective view of an embodiment of a reusable assembly as a reusable holder of a cell for simultaneous electrochemical and EPR measurements according to the present invention.

Referring to FIGS. 1-3, a cell 50 having removable and disposable assemblies for simultaneous, or approximately simultaneous, electrochemical and electron paramagnetic resonance (EPR) spectroscopic measurements is shown. The cell 50 includes a first hollow tube assembly 10 and a second hollow tube assembly 30. The cell 50 is arranged in a two electrode configuration that allows for the reduction or oxidation of a compound or other sample to be analyzed that is placed within the cell 50 when a potential is applied to the reference electrode 52, such as from a reference voltage source 19. The cell 50 is further capable of being placed within a cavity of an EPR spectrometer for free radical analysis.

Reference electrode 52 can be made from silver or silver chloride, for example, or other suitable material, such as may depend upon the use or application. A potential is applied to the reference electrode 52, which partially extends out from an upper portion 34 of the second hollow tube assembly 30, the second hollow tube assembly 30 being the disposable portion of the cell 50. The reference electrode 52 is responsible for carrying the potential into the electrolyte and analyte solution mixture 42 placed in the second hollow tube assembly 30. The electrolyte can be a buffer, an acid, or a base in an aqueous or non-aqueous solution for example. The analyte is the substance of interest that will be analyzed by one or both of an EPR spectrometer and an electroanalysis process. Such substances of interest as the analyte can include therapeutic pharmaceutical compounds, such as Ketoconazole (KTZ), for example, but the substances of interest for analysis can include various suitable substances for analysis, and should therefore not be construed in a limiting sense. KTZ is a common drug for the treatment of fungal infections of the mouth, skin, and urinary tract, among others.

Referring to FIG. 2, the second hollow tube assembly 30 is shown. The second hollow tube assembly includes a second hollow tube 32 that can be a simple capillary glass tube, such as with a volume of 75-100 µL, for example. However, the second hollow tube 32 can be made from any other suitable material, such as quartz, and can have a different volume depending on the use or application, and the type, material or size of the second hollow tube 32 should not be construed in a limiting sense. The second hollow tube 32 has an upper portion 34 and the lower portion 36. The lower portion 36 of the second hollow tube 32 is sealed by a second insulating material 38. The second insulating material 38 acts as a place holder for a working electrode 40 and also as a stopper to create a chamber within the interior of the second hollow tube 32. Disposed within the interior of the second hollow tube 32 is an electrolyte solution that can be a buffer, an acid, or a base. The electrolyte solution can take the form of an aqueous or non-aqueous solution, for example.

Added to the electrolyte solution in the second hollow tube 32 is an analyte, the substance that is to be tested or analyzed. As discussed, the analyte can be any common therapeutic pharmaceutical compound to be oxidized or reduced for the analysis, such as Ketoconazole (KTZ). When a sample of KTZ is oxidized, the unpaired electrons can generate EPR signals when placed within an EPR spectrometer. Further, when KTZ is oxidized, it can also provide electrochemical data for electroanalysis.

The second hollow tube assembly 30, which typically can be a disposable assembly, is arranged to be removably insertable into the interior of the first hollow tube assembly 10, which typically can be a reusable holder for the second hollow tube assembly 30. Once the electrochemical reaction has been completed and the necessary spectroscopic and electroanalytical data has been collected, the second hollow tube assembly 30 can be removed from within the interior of the first hollow tube assembly 10. The used second hollow tube assembly 30 can then be discarded, for example. If a new analysis or a different analysis is to be performed, a new, disposable second hollow tube assembly 30 is typically used to enhance the accuracy and reliability of the analysis, in that contaminants from a previous analysis are likely not present in a previously unused disposable second hollow tube assembly 30, as well as the use of materials in forming the second hollow tube assembly 30 typically have a relative low cost, for example.

The working electrode 40 extends out from the second hollow tube assembly 30 and through a second insulating material 38. The second insulating material 38 can be made from a number of suitable materials, including plastic, rubber, or thread seal tape, commonly referred to as "Teflon® tape," and should not be construed in a limiting sense. Thread seal tape is typically a polytetrafluoroethylene (PTFE) film common for use in sealing pipe threads and tubes. The second insulating material 38 is positioned in the lower portion 36 of the second hollow tube assembly 30 creating and acting as a seal for a chamber formed within the interior of the second hollow tube 32 so that the electrolyte and analyte solution can be stored within the second hollow tube 32.

Figure 5:
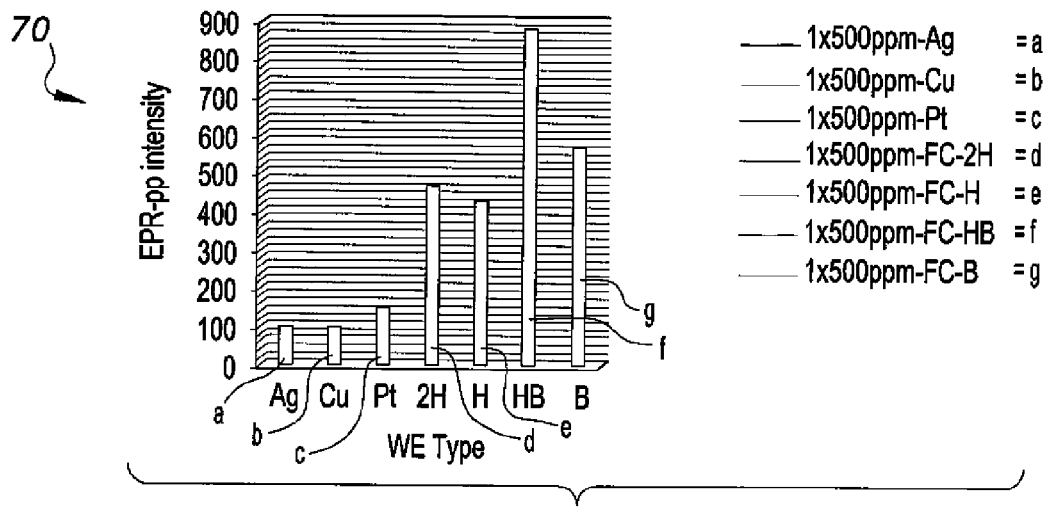
FIG. 5 is a histogram graph of EPR signal strength generated by analysis using embodiments of a cell having reusable and disposable assemblies for simultaneous electrochemical and EPR measurements according to the present invention involving the oxidation of 50 µg/mL Ketoconazole in 0.1 mol·dm−3 sulfuric acid electrolyte solution with different working electrode materials.

The working electrode 40 is disposed within the interior of the second hollow tube 32. The working electrode 40 extends into the interior of the second hollow tube 32 and extends out from the lower portion 36 of the second hollow tube 32. The working electrode 40 can be composed from a number of different materials, including base metals, such as copper, precious metals, such as gold, silver or platinum, allotropes of carbon, or any other suitable conductive material, and should not be construed in a limiting sense. Desirably, the working electrode 40 is composed from graphite, an allotrope of carbon, for example. Further, for optimum reduction-oxidation reactions, graphite pencil lead is relatively more desirable. In this regard, as to the working electrode 40, graphite pencil lead is typically classified in terms of hardness grades. Hardness grades are associated on a hardness scale with the letter H or B or a combination of both, HB. The letter "H" is recognized as hard while the letter "B" is recognized as soft. The grade of HB is the common type of writing pencil used by students. The grade of a pencil can be displayed as successive letters, such as HH (2H) for harder, and BB (2B) for softer pencil leads. Typically, the more letters present, the harder or softer the pencil lead. For example, a graphite pencil lead graded HH (2H) is harder than a graphite pencil lead graded as H. A graphite pencil lead graded BB (2B) is softer than a graphite pencil lead graded as B. As shown in FIG. 5, graphite pencil lead was relatively superior as a working electrode material for the working electrode 40 for producing relatively stronger EPR signal intensity values in comparison to base metals and precious metals used to form the working electrode 40.

Referring to FIG. 3, an embodiment of the first hollow tube assembly 10 is shown, which can be used as a reusable holder, for example. A first hollow tube 12 having an upper portion 14 and a lower portion 16 is composed from EPR quartz glass. EPR quartz is a clear fused quartz. Clear fused quartz is desirable for use as opposed to other forms of glass as, for example, soda-lime glass or borosilicate glass. These other forms of glass, such as soda-lime glass or borosilicate glass, absorb microwaves and spoil the Q of the resonator, which can make tuning difficult and can skew the data. The inner diameter of the first hollow tube 12 can be any size, dependent on the use or application as, for example, having an inner diameter of 3 mm, and should not be construed in a limiting sense.

At the lower portion 16 of the first hollow tube 12 is an electro-conductive material 18 deposited within the interior of the first hollow tube 12. The electro-conductive material 18 carries the potential from the working electrode 40 to a wire connector 22. The electro-conductive material 18 can be of any suitable form, such as in the form of either a conducting paste or a conducting liquid, for example. The electro-conductive material can also be made from a number of various materials, including a carbon paste or a liquid mercury, for example. When the second hollow tube assembly 30 is inserted within the interior of the first hollow tube assembly 10 to form the cell 50, the working electrode 40 engages with the electro-conductive material 18. The cell 50, for example, including the first hollow tube assembly 10, typically as a reusable assembly and holder, and including the second hollow tube assembly 30, typically as a disposable assembly, when combined, can be considered a whole cell for simultaneous electrochemical and EPR measurements.

Adjacent to the electro-conductive material 18 within the interior of the lower portion 16 of the first hollow tube 12 is a first insulating material 20. The first insulating material closes off the aperture at the end of the lower portion 16 of the first hollow tube 12 and creates a chamber within the interior of the first hollow tube 12. The first insulating material 20, similar to the second insulating material 38, can be composed from various materials, including plastic, rubber, or thread seal tape, commonly referred to as "Teflon® tape," and should not be construed in a limiting sense. The first insulating material 20 creates a chamber and acts to seal the chamber within the interior of the first hollow tube 12 that receives the disposable second hollow tube assembly 30.

Originating outside the first hollow tube 12 and extending through the first insulating material 20 and into the lower portion 16 to engage with the electro-conductive material 18 is a wire connector 22. The wire connector 22 communicates the potential from the working electrode 40 that is carried by the electro-conductive material 18 to a measurement device 54. The wire connector 22 can be made from a number of various materials, including copper, or any other suitable conductive material, for example. Also, the wire connector can also be of various suitable types and shapes, such as a plug type connector or a wire type connector, for example. The measurement device 54 can be a number of various measuring devices, including a potentiostat, an ammeter, a voltmeter, or a multi-meter, among others, for example. By the wire connector 22 being engaged with the electro-conductive material 18, various electrochemical measurements can be taken and determined, such as values of accumulation voltages or currents that are acting upon the working electrode 40, for example.

Once the second hollow tube assembly 30 is placed in association with the first hollow tube 12 of the first hollow tube assembly 10, the working electrode 40, extending out from the lower portion 36 of the second hollow tube 32 of the second hollow tube assembly 30, engages with the electro-conductive material 18 located in the lower portion 16 of the first hollow tube 12. Also engaged with the electro-conductive material 18 is the wire connector 22. The wire connector 22 enters the lower portion 16 of the first hollow tube 12 through the first insulating material 20 and engages with the electro-conductive material 18.

When the potential from the generated reference voltage from the reference voltage source 19 is applied to the reference electrode 52, the generated potential enters the electrolyte and analyte solution mixture 42, and a reduction-oxidation (Redox) reaction occurs. Also, when the potential is carried into the electrolyte and analyte mixture 42, an electrochemical reaction of interest for an analysis occurs at the working electrode 40 disposed within the second hollow tube 32 of the second hollow tube assembly 30. As the potential is applied, an accumulation voltage acts upon the working electrode 40. The electro-conductive material 18 communicates this electric potential to the wire connector 22. The measurement device 54, in communication with the wire connector 22, measures the voltage and current acting upon the working electrode 40, for example.

Continuing with reference to FIGS. 1-6, the cell 50 is also insertable into an EPR spectrometer for EPR spectroscopy analysis. Typically, the cell 50 is placed within a cavity of the EPR spectrometer. Surrounding the cavity is a plurality of magnets that generate an electro-magnetic field. When the oxidation or reduction reaction occurs on the sample, free radicals of the sample, i.e. unpaired electrons, will be exposed. Since unpaired electrons naturally have a charge and when the unpaired electrons spin they create a random magnetic moment, the free radical electrons line up with the electromagnetic field generated by the magnets surrounding the cavity. A microwave generator, typically a Klystron, pulses the lined up free radicals with short bursts of microwaves. These microwaves are absorbed and transmitted through the sample to a receiver that is typically located on the other end of the spectrometer. The receiver will then translate the data received into spectra showing signal strength intensity in relation to the applied magnetic field. The spectra can be plotted by a computer or processor connected to the receiver, for example.

Figure 4:
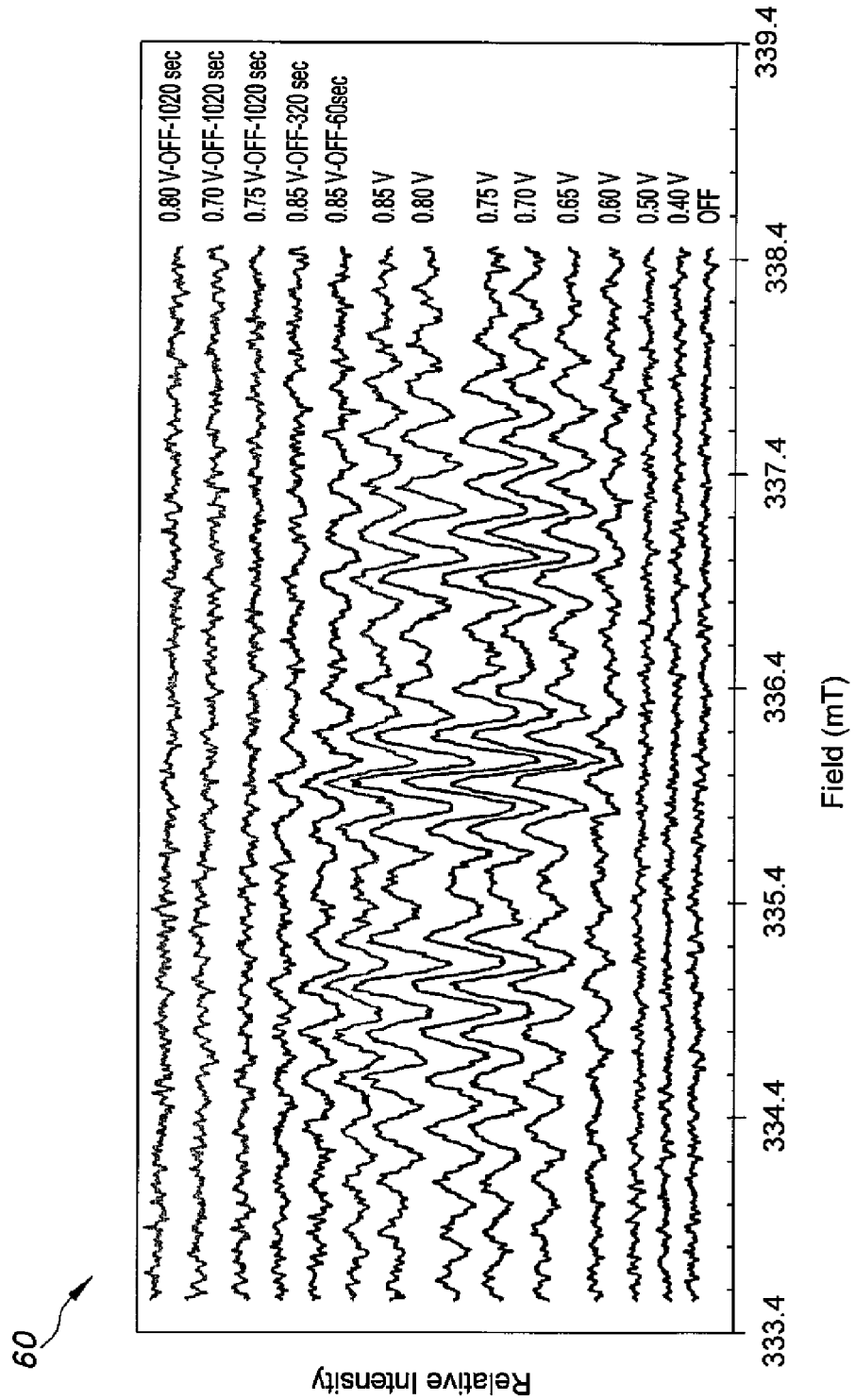
FIG. 4 is a graph of EPR experimental spectra generated by analysis using embodiments of a cell having reusable and disposable assemblies for simultaneous electrochemical and EPR measurements according to the present invention involving the oxidation of 50 µg/mL Ketoconazole in 0.1 mol·dm$^{-3}$ sulfuric acid electrolyte solution at different accumulation voltages using as a working electrode HB graded graphite pencil lead.

Referring now to FIG. 4, EPR experimental spectra are shown in the graph 60 of spectra for the oxidation reaction of 50 μg/mL of the pharmaceutical drug Ketoconazole in a 0.1 mol·dm$^{-3}$ sulfuric acid electrolyte solution with different accumulation voltages using a graphite pencil lead as the working electrode. The grade for the graphite pencil lead in this experiment is HB. As shown in FIG. 4, relatively no reaction signal intensity occurred from 0.40V to 0.50V. Starting at a potential of 0.60V, the signal intensity from the Ketoconazole continued to increase up until 0.85V. The signal strength began to decline as the voltage was decreased and the time the potential was shut off ("OFF" in FIG. 4) was increased. FIG. 4 shows that signal intensity is greatest for a FIB graphite pencil lead working electrode when the applied potential is between 0.65V to 0.85V, for example.

Referring to FIG. 5, EPR experimental signal strengths are shown for the oxidation reaction of 50 μg/mL of the pharmaceutical drug Ketoconazole in a 0.1 mol·dm$^{-3}$ sulfuric acid electrolyte solution, each at a concentration of 1×500 ppm, for example, with different materials composing the working electrode types. The materials used for the working electrode ("WE") were (a) silver, (b) copper, (c) platinum, (d) 2H graded graphite pencil lead, (e) H graded graphite pencil lead, (f) HB graded graphite pencil lead, and (g) B graded graphite pencil lead. The experimental data of the histogram graph 70 of FIG. 5 shows that not all working electrode types provided equal oxidation reactions. As seen by the graph, copper and silver provide for the relatively weakest signal strength, while the other metals, such as platinum, provided relative minimal signal strength. Further, using graphite pencil lead, working electrode types, 2H grade and H grade provided relatively moderate signal strengths. A B graded graphite pencil lead provided relative increased signal strength over the harder graded counterpart leads. However, as shown in the histogram graph 70, an HB graded graphite pencil lead, which is a mixture of hard and soft leads, provided the greatest relative signal strength intensity.

Figure 6:
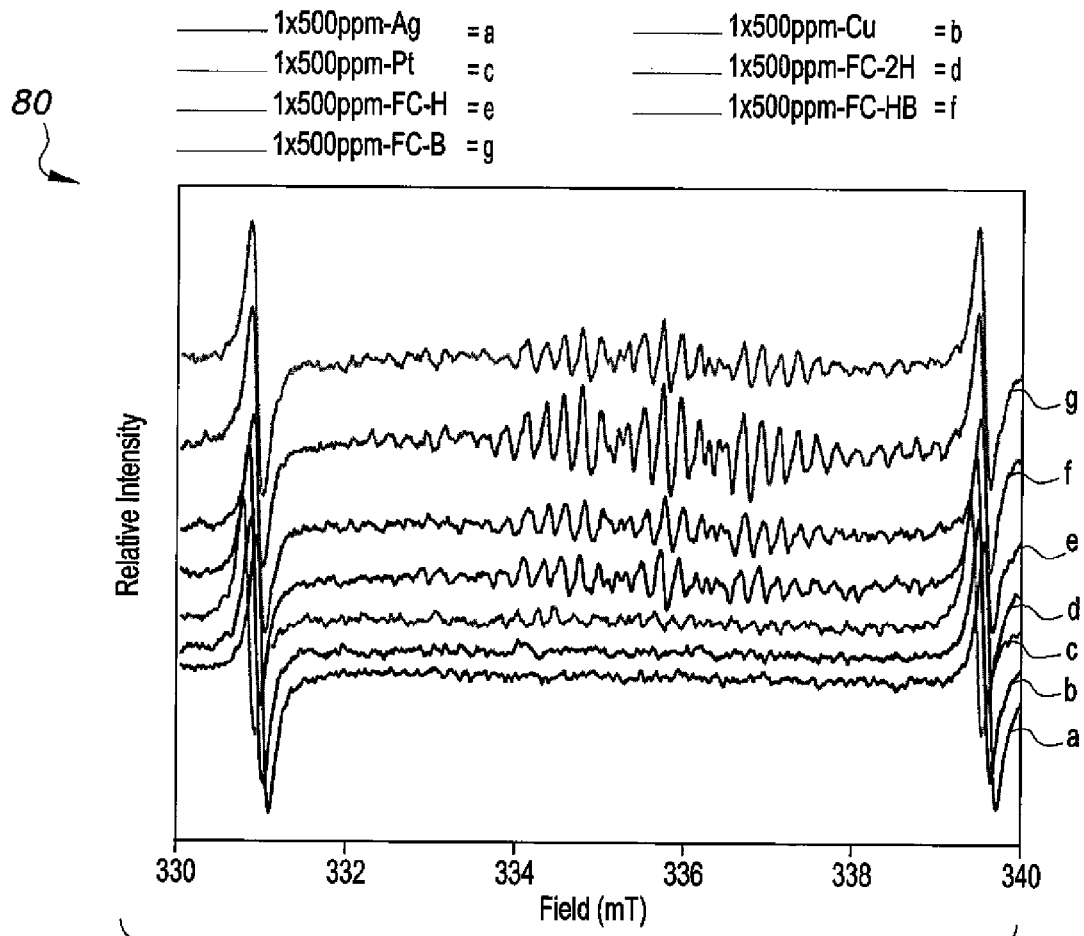
FIG. 6 is a graph of EPR experimental spectra generated by analysis using embodiments of a cell having reusable and disposable assemblies for simultaneous electrochemical and EPR measurements according to the present invention involving the oxidation of 50 µg/mL Ketoconazole in 0.1 mol·dm$^{-3}$ sulfuric acid electrolyte solution with different working electrode materials.

Referring to FIG. 6, EPR experimental spectra corresponding with the data of the FIG. 5 histogram graph 70 are shown in the graph 80 of spectra for the oxidation reaction of 50 μg/mL of the pharmaceutical drug Ketoconazole in a 0.1 mol·dm$^{-3}$ sulfuric acid electrolyte solution, each at a concentration of 1×500 ppm, for example, with different materials composing the working electrode types (with satellite peaks of Mn(II) as an external reference material). As shown in the graph 80 of spectra of FIG. 6, similar to the results of histogram graph 70 of FIG. 5, the signal strength generally increases when the working electrode is composed of a graphite pencil lead as opposed to a base metal or a precious metal working electrode. The silver and copper working electrodes again provided for the weakest relative signal strength, while the platinum working electrode provided relative minimal signal strength. The graphite pencil lead working electrodes, on the other hand, provided improved relative signal strength when the applied magnetic field was between 334 milliTeslas (mT) and 336 mT, for example. HB graded graphite pencil lead once again provided for the greatest relative signal strength. Therefore, the experimental results illustrated by the histogram graph 70 of FIG. 5 and the graph 80 of spectra of FIG. 6 show that a graphite pencil lead working electrode, as to working electrode 40, can provide optimal oxidation values for an electrochemical reaction and for EPR spectroscopy. It is to be noted that any of various manufactured graphite pencil leads can be used, such as including those manufactured by Faber-Castell and Pentel Co. Ltd., among others. For the above experiments Faber-Castell ("FC") graphite pencil leads were used.

It is to be understood that the present invention is not limited to the embodiments described above, but encompasses any and all embodiments within the scope of the following claims.

We claim:

1. A cell for electrochemical and Electron Paramagnetic Resonance (EPR) measurements, comprising:
   a first hollow tube assembly, the first hollow tube assembly having a first hollow tube, the first hollow tube having an electro-conductive material positioned within a lower portion of the interior of a first hollow tube and having a first insulating material positioned adjacent to the electro-conductive material within the interior of the first hollow tube, the first insulating material acting as a first seal;
   a wire connector, the wire connector positioned to enter the lower portion of the interior of the first hollow tube extending through the insulating material and engaging the electro-conductive material;
   a second hollow tube assembly, the second hollow tube assembly removably positioned within the first hollow tube assembly in forming the cell, the second hollow tube assembly having a second hollow tube having a second insulating material situated within a lower portion of the interior of the second hollow tube acting as a second seal, the second hollow tube to contain within the interior of the second hollow tube a supporting electrolyte including a sample for analysis;
   a working electrode, the working electrode positioned within the interior of the second hollow tube extended through the second insulating material and extending out through the second hollow tube to position into the electro-conductive material; and a reference electrode, the reference electrode being adapted to be removably positioned within the interior of the second hollow tube and extending out through an opening at an upper portion of the second hollow tube in opposing relation to the working electrode.

2. The cell according to claim 1, wherein the reference electrode is comprised of a material selected from the group consisting of silver and silver chloride, and the wire connector is comprised of copper.

3. The cell according to claim 1, wherein the wire connector is comprised of copper.

4. The cell according to claim 1, wherein the electro-conductive material is comprised of at least one of a liquid mercury or a graphite carbon paste.

5. The cell according to claim 1, wherein the first insulating material and the second insulating material are each comprised of thread seal tape.

6. The cell according to claim 1, wherein the working electrode is comprised of graphite.

7. The cell according to claim 6, wherein the graphite is comprised of a graphite pencil lead.

8. The cell according to claim 7, wherein a grade of the graphite pencil lead is selected from the group consisting of an H grade, a B grade, a 2H grade, and a HB grade.

9. A method for preparing a cell for electrochemical analysis and Electron Paramagnetic Resonance (EPR) spectroscopy, comprising the steps of:
providing a first hollow tube assembly having a first hollow tube and an electro-conductive material adjacently positioned to a first insulating material sealing an aperture in a lower portion of the first hollow tube engaged with a wire connector positioned through the first insulating material mad into the electro-conductive material;
providing a removable second hollow tube assembly having a second hollow tube and a second insulating material sealing an aperture in a lower portion of the second hollow tube engaged with a working electrode positioned in an interior of the second hollow tube and through the second insulating material;
setting the removable second hollow tube assembly within an interior of the first hollow tube of the first hollow tube assembly to combine the first hollow tube assembly and the second hollow tube assembly to form a cell and to communicatively connect the working electrode to the electro-conductive material within the lower portion of the first hollow tube and to the wire connector through the electro-conductive material; and
positioning a reference electrode into the interior of the second hollow tube to extend out through an opening at an upper portion of the second hollow tube in opposing relation to the working electrode.

10. The method for preparing a cell according to claim 9, wherein the reference electrode is comprised of a material selected from the group consisting of silver and silver chloride, and the wire connector is comprised of copper.

11. The method for preparing a cell according to claim 9, wherein the wire connector is comprised of copper.

12. The method for preparing a cell according to claim 9, wherein the electro-conductive material is comprised of at least one of a liquid mercury or a graphite carbon paste.

13. The method for preparing a cell according to claim 9, wherein the first insulating material and the second insulating material are each comprised of thread seal tape.

14. The method for preparing a cell according to claim 9, wherein the working electrode is comprised of graphite.

15. The method for preparing a cell according to claim 9, wherein the graphite is comprised of a graphite pencil lead.

16. The method for preparing a cell according to claim 15, wherein a grade of the graphite pencil lead is selected from the group consisting of an H grade, a B grade, a 2H grade, and a HB grade.

17. A method for preparing a sample for simultaneous electrochemical analysis and Electron Paramagnetic Resonance (EPR) spectroscopy, comprising the steps of:
providing a first hollow tube assembly having a first hollow tube and an electro-conductive material adjacently positioned to a first insulating material sealing an aperture in a lower portion of the first hollow tube engaged with a wire connector positioned through the first insulating material and into the electro-conductive material;
providing a removable second hollow tube assembly having a second hollow tube and a second insulating material sealing an aperture in a lower portion of the second hollow tube engaged with a working electrode positioned in an interior of the second hollow tube and through the second insulating material;
setting the removable second hollow tube assembly within an interior of the first hollow tube of the first hollow tube assembly to combine the first hollow tube assembly and the second hollow tube assembly to form a ceil and to communicatively connect the working electrode to the electro-conductive material within the lower portion of the first hollow tube and to the wire connector through the electro-conductive material;
dispensing an electrolyte solution into the interior of the second hollow tube;
adding an analyte to be analyzed into the electrolyte solution placed within the interior of the second hollow tube;
inserting a reference electrode into the interior of the second hollow tube to extend out through an opening at an upper portion of the second hollow tube in opposing relation to the working electrode; and
applying a potential to the reference electrode to generate an electrochemical reaction to analyze the analyte.

18. A method for preparing a sample according to claim 17, further comprising the steps of:
placing the formed cell including the combined first hollow tube assembly and the removable second hollow tube assembly within an EPR spectrometer; and
performing EPR spectroscopy on the analyte while generating the electrochemical reaction to analyze the analyte.

* * * * *